United States Patent [19]

Furuta et al.

[11] Patent Number: 4,668,617

[45] Date of Patent: * May 26, 1987

[54] APPARATUS AND METHOD FOR OPTICALLY ANALYZING A PLURALITY OF ANALYSIS ITEMS IN A SAMPLE IN A CONTAINER

[75] Inventors: Yoshiteru Furuta, Katsuta; Yasushi Nomura, Mito, both of Japan

[73] Assignee: Hitachi, Ltd., Tokyo, Japan

[*] Notice: The portion of the term of this patent subsequent to Feb. 2, 1999 has been disclaimed.

[21] Appl. No.: 574,586

[22] Filed: Jan. 27, 1984

Related U.S. Application Data

[63] Continuation of Ser. No. 268,372, May 29, 1981, abandoned.

[30] Foreign Application Priority Data

Jun. 30, 1980 [JP] Japan ............................. 55-71374
Sep. 3, 1980 [JP] Japan ............................ 55-121093

[51] Int. Cl.$^4$ ..................... G01N 35/06; C12Q 1/60; C12Q 1/28
[52] U.S. Cl. ......................................... 435/4; 422/64; 422/65; 422/67; 435/11; 435/16; 435/19; 435/24; 435/26; 435/28
[58] Field of Search ................. 435/4, 11, 16, 18, 19, 435/24, 25, 26, 28, 291, 808, 288; 422/64, 65, 67, 72

[56] References Cited

U.S. PATENT DOCUMENTS

| 4,158,545 | 6/1979 | Yamashita et al. | 436/47 |
| 4,276,051 | 6/1981 | Ginsberg et al. | 422/64 |
| 4,313,735 | 2/1982 | Yamashita et al. | 422/67 |
| 4,338,279 | 7/1982 | Orimo et al. | 422/65 |

FOREIGN PATENT DOCUMENTS

| 52-40189 | 3/1977 | Japan | 422/64 |
| 56-154666 | 11/1981 | Japan | 422/64 |
| 56-168554 | 12/1981 | Japan | 422/64 |

Primary Examiner—Michael S. Marcus
Attorney, Agent, or Firm—Antonelli, Terry & Wands

[57] ABSTRACT

An apparatus and method for analyzing at least two analytical items in a sample solution in a single container, wherein a series of transparent containers supported on a rotatable disc pass over a sample-receiving position, a first reagent solution-adding position, a second reagent solution-adding position, an optical path of a photometer, a solution-discharging device and a washing device. In the sample-receiving position, a fixed volume of sample is introduced into one of the transparent containers. In the first reagent solution-adding position, the first reagent solution is introduced into the transparent container, whereby a reaction is allowed to proceed. Subsequently, the container is passed across an optical path, and absorbance of light by the reaction solution is measured, to provide first measurements. Thereafter, a second reagent solution is introduced into the transparent container at the second reagent solution-adding position, without removal of the first reaction solution, whereby a further reaction is allowed to proceed. Subsequently, the container is passed across an optical path, and absorbance of light by the resulting solution in the transparent container is measured, to provide second measurements. The first analytical item can be investigated from the first measurements, and the second analytical item can be investigated from differences between the first and second measurements.

19 Claims, 6 Drawing Figures

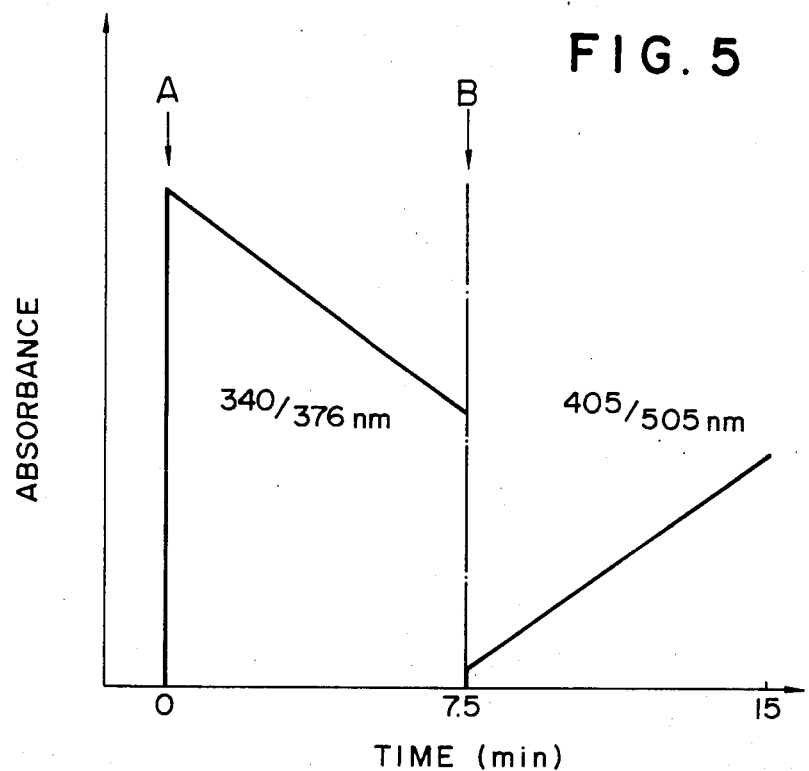

APPARATUS AND METHOD FOR OPTICALLY ANALYZING A PLURALITY OF ANALYSIS ITEMS IN A SAMPLE IN A CONTAINER

This is a continuation of application Ser. No. 268,372, filed May 29, 1981, abandoned.

BACKGROUND OF THE INVENTION

This invention relates to a method and apparatus for optically analyzing a plurality of items, particularly a method and apparatus for analyzing a plurality of items by subjecting a sample to enzyme reaction, and then determining the result or progress of the enzyme reaction by a photometer.

In the quantitative analysis of a sample containing many components, particularly that of a metabolic material in body fluid such as blood, analytical methods utilizing an enzyme which acts specifically on a metabolic material have been recently employed. An enzyme reaction proceeds under very mild conditions in a short time. Enzymes have a property of acting merely on a specific material even if it contains many contaminants. Analytical methods utilizing an enzyme reaction having such advantages are employed for biochemical inspection in hospitals, etc.

Conventional photometric methods utilizing an enzyme reaction are generally directed to quantitative analysis of only one analysis item in one sample placed in one reactor vessel, as disclosed, for example, in U.S. Pat. No. 3,838,010.

SUMMARY OF THE INVENTION

An object of the present invention is to provide a method and apparatus for optical analysis where a plurality of items can be quantitatively determined for a sample placed in a vessel.

Another object of the present invention is to provide a method and apparatus for optical analysis where only a very small amount of a sample is enough for the analysis of a plurality of items.

A further object of the present invention is to provide an efficient analytical method and apparatus where sampling number can be decreased, so that second or successive sampling operation can be omitted for further analysis items.

A still further object of the present invention is to provide an analytical method and apparatus where a plurality of enzyme reactions are utilized for analyzing a plurality of items, and thus the reaction of the first analysis item does not interfere with the reaction of the second analysis item, resulting in very small error in measurement.

The present invention provides a method and apparatus where a plurality of enzyme reactions are made to take place sequentially in one vessel; optical characteristics of each reaction solution is measured; the first analysis item is obtained on the basis of the first enzyme reaction; and the second analysis item on the basis of the second enzyme reaction.

According to one of the desirable embodiments of the present invention, a reagent solution containing an enzyme is added to a sample solution to cause enzyme reaction, and the result of reaction is determined by colorimetric end point method.

According to another desirable embodiment of the present invention, a reagent solution containing a substrate is added to a sample solution to cause enzyme reaction of the substrate with an enzyme contained in the sample solution, and the progress of reaction is determined by rate assay method. Therefore, the concept "concentrations of analysis items" according to the present invention covers the content of components in a sample and the activity of an enzyme in a sample.

According to the desirable embodiment of the present invention, the absorbance of a first reaction solution resulting from the addition of a first reagent solution is measured, and then a second reagent solution is added to the first reaction solution to obtain a second reaction solution. The concentration of a first analysis item is obtained on the basis of the absorbance of the first reaction solution. The concentration of the second analysis item is obtained on the basis of the absorbance of the second reaction solution and the absorbance of the first reaction solution. In that case, the volume of the second reaction solution is larger than that of the first reaction solution, and thus, in order to calculate the concentration of the second analysis item from signals based on both reaction solutions, the absorbance values corrected on an assumption that both reaction solutions have equal volumes are used. That is, either absorbance is to be corrected in accordance with the degree of dilution of the first reaction solution due to the addition of the second reagent solution.

BRIEF DESCRIPTION OF THE DRAWINGS

FIG. 5 is a diagram showing a reaction process in the analysis of lactic acid dehydroenzyme (LDH) and leucine aminopeptidase (LAP).

FIG. 6 is a diagram showing a reaction process in the analysis of glutamic oxalacetic transaminase (GOT) and glutamic pyruvic transaminase (GPT).

DETAILED DESCRIPTION OF THE PREFERRED EMBODIMENT

Several examples of applying an enzymatic analytical method to a serum sample will be described below before describing the embodiments according to the present invention.

At first, glucose in serum undergoes the following reaction:

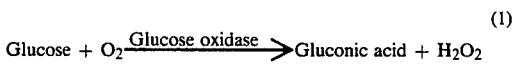

$$\text{Glucose} + O_2 \xrightarrow{\text{Glucose oxidase}} \text{Gluconic acid} + H_2O_2 \quad (1)$$

Cholesterol includes an ester form and a free form, and each form undergoes the following reaction. Whole cholesterol is the total of the two forms:

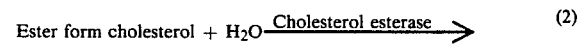

$$\text{Ester form cholesterol} + H_2O \xrightarrow{\text{Cholesterol esterase}} \quad (2)$$

$$\text{Free form cholesterol} + \text{Fatty acid}$$

$$\text{Free form cholesterol} + O_2 \xrightarrow{\text{Cholesterol oxidase}} \quad (3)$$

-continued

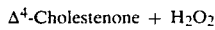

Neutral fat undergoes the following reaction:

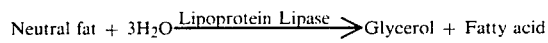  (4)

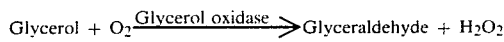

Phospholipids undergo the following reaction:

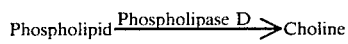  (6)

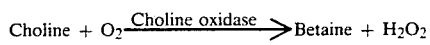  (7)

Hydrogen peroxide ($H_2O_2$) produced in the above-mentioned reactions according to formulae (1), (3), (5) and (7) undergoes reaction according to the following formula (8) by action of peroxidase to produce a red pigment, and thus the reaction can be traced by monitoring by photometer.

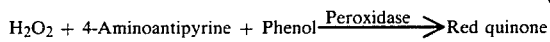  (8)

EXAMPLE 1

Figure 1:
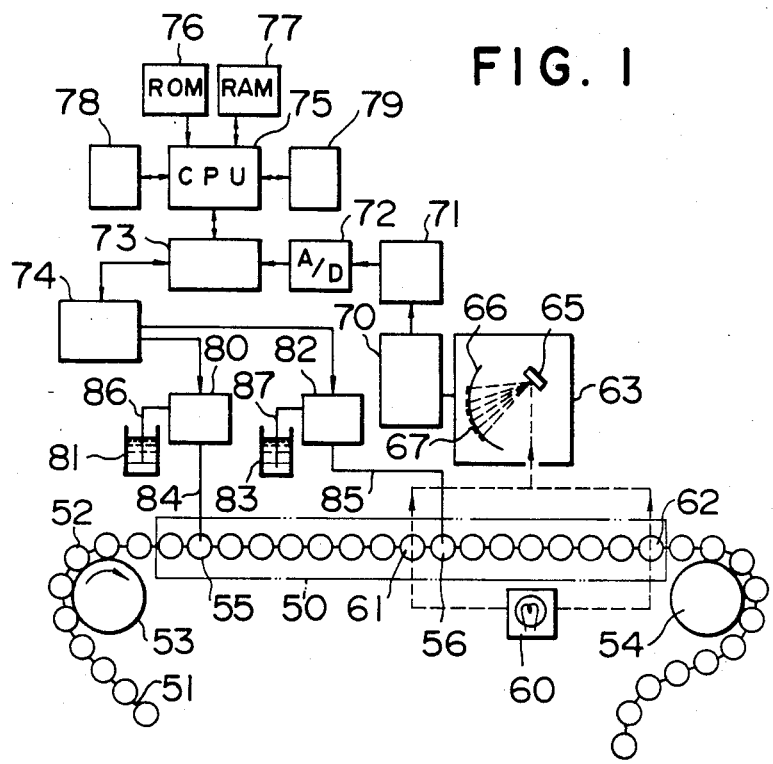
FIG. 1 is a flow diagram schematically showing a structure of one embodiment according to the present invention.

FIG. 1 is a flow diagram schematically showing a structure of the analytical apparatus according to one embodiment of the present invention. When two items of glucose and whole cholesterol are to be analyzed, a first reagent solution containing glucose oxidase, peroxidase, 4-aminoantipyrine, phenol and the like, which are necessary for the above-mentioned reactions of formulae (1) and (8), is added to a predetermined amount of a sample, and after the completion of the reactions of formulae (1) and (8), the absorbance of first reaction solution is measured by colorimetric method, and the concentration of glucose is calculated from the thus obtained absorbance value. Subsequently, a second reagent solution containing enzymes such as cholesterol esterase, cholesterol oxidase and the like, which are necessary for the reactions of formulae (2) and (3), is added to the above-mentioned first reaction solution. Consequently, the reactions of formulae (2), (3) and (8) take place. For the peroxidase required for the reaction of formula (8), the remaining portion of the first reagent solution is used. After the completion of the reactions of formulae (2), (3) and (8), the absorbance of second reaction solution is measured. The difference between the now obtained absorbance datum and the previously obtained one is proportional to the concentration of whole cholesterol.

Likewise, any of two items can be selected from the glucose, whole cholesterol, free cholesterol, neutral fat and phospholipids, and can be analyzed in one and same reactor vessel by single sampling.

The structure shown in FIG. 1 will be explained below. A flexible chain 51 is loaded with a large number of transparent reactor vessels 52. The chain 51 is comprised of a large number of detachable cylindrical holders rotatably connected to one another. Each of the reactor vessels 52 containing a liquid sample such as a serum sample is charged into each of the holders, and conveyed in a horizontal direction by means of driving sprockets 53 and 54. Both ends of chain 51 may be connected to each other or separated from each other. Chain 51 moves over thermostat bath 50 containing a liquid at a predetermined temperature, while the reactor vessels are conveyed while their lower parts are immersed in thermostat bath 50. Over thermostat bath 50, there are reagent-adding positions 55 and 56 and photometric positions 61 and 62.

Light beam from a light source 60 is divided in two beams by a mirror system, cast onto the reactor vessels at photometric positions 61 and 62 immersed in the thermostat liquid through light-transmitting windows provided on the side wall of thermostat bath 50, passed through the side wall on the opposite side and led to multi-wavelength photometer 63 equipped with a concave diffraction grating 65 through one light pass.

Though not shown in the drawing, the light beam having passed through photometric position 61 and the light beam having passed through photometric position 62 are time-shared from each other by a sector or the like, and led to photometer 63 alternately.

A plurality of semiconductor light detectors 67 are arranged at positions corresponding to the respective measuring wavelengths on Rowland's circle 66 of multi-wavelength photometer 63. Electric signal from either light detector is selected by wavelength selector 70, and thier differential signal is obtained by means of differential amplifier 71. The differential signal is converted into a digital signal by A-D converter 72, and led through interface 73 to central processing unit 75 for carrying out necessary processings.

First dispenser 80 and second dispenser 82 are connected to central processing device 75 through interface 74 and interface 73 of controlling mechanism. Analysis items are input into the central processing unit from operating panel 78, and the measured analytical results are displayed on display part 79. Reading-out-memory (ROM) 76 and random access memory (RAM) 77 are provided on central processing unit 75.

First dispenser 80 is provided with discharge pipe 84 extendable over to reagent-adding position 55 and suction pipe 86 insertable into enzyme-containing first reagent solution tank 81. Second dispenser 82 is provided with discharge pipe 85 extendable over to reagent-adding position 56 and suction pipe 84 insertable into enzyme-containing second reagent solution tank 83. In analyzing both items of glucose and whole cholesterol by apparatus of FIG. 1, a first enzyme reagent solution and a second enzyme reagent solution having the following compositions are used.

Composition of first enzyme reagent solution:

| | |
|---|---|
| Phosphate buffer (pH 7.0) | 100 m mole/liter |
| Glucose oxidase | 18 U/ml |
| Peroxidase | 1.2 U/ml |
| 4-Aminoantipyrine | 0.8 m mole/ml |
| Phenol | 11 m mole/liter |

Composition of second enzyme reagent solution:

| | |
|---|---|
| Phosphate buffer (pH 7.7) | 5 moles/liter |
| Cholesterol esterase | 2 U/liter |
| Cholesterol oxidase | 3 U/liter |

-continued

| Methanol | 10 moles/liter |
|---|---|
| Hydroxypolyethoxydodecane | 4% |

In analyzing glucose and whole cholesterol, the amount of serum sampled into reactor vessel 52 is 5 μl; the amount of the first enzyme reagent solution to be added is 500 μl; and the amount of the second enzyme reagent solution to be added is 50 μl. Absorbance is measured by single beam dual wavelength method. The wavelengths selected by wavelength selector 70 are 505 nm and 600 nm. Temperature of thermostat bath 50 is maintained at 37° C.

Serum sample is placed in reactor vessel made of transparent material, and then the reactor vessel is loaded onto chain 51.

A vessel for reagent blank and a vessel containing the standard sample of glucose and that of whole cholesterol are placed at the head of a series of reactor vessels for sample. Before the measurement of analysis sample, working curves for both analysis items are obtained from the measured values of the reagent blank and the standard samples.

When chain 51 moves and reactor vessel 52 containing the serum sample reaches first reagent-adding position 55, first dispenser 80 is operated and first enzyme reagent solution is charged into the reactor vessel from discharge pipe 84.

The sample thus mixed with the reagent solution immediately undergoes reaction according to formulae (1) and (8). When reactor vessel 52 is intermittently conveyed to photometric point 61, light is cast onto the reactor vessel from light source 60, and the transmitted light is dispersed into spectra by concave diffraction grating 65 of multi-wavelength photometer 63, and the intensity of specific wavelength light is measured. The signal of light intensity serves to calculate the corresponding glucose concentration on the basis of the working curve obtained in advance and the glucose concentration is displayed on display part 79. When the same reactor vessel advances by one more step and reaches second reagent-adding position 56, second dispenser 82 is put into operation and the second enzyme reagent solution is charged into the reactor vessel from discharge pipe 85, and then the sample solution thus admixed immediately undergoes reactions according to formulae (2), (3) and (8). When the reactor vessel is intermittently conveyed to photometric position 62, light is cast onto the reactor vessel from light source 60, and the transmitted light is dispersed into spectra by multi-wavelength photometer, and a signal based on the light intensity of same specific wavelength light as above is obtained. The signal value based on the light intensity measured for the same sample at photometric position 61 prior to the addition of the second enzyme reagent solution has been memorized by RAM, and therefore a difference between the memorized signal value and the signal value now obtained due to the reaction caused by the addition of the second enzyme reagent is proportional to the concentration of whole cholesterol. Accordingly, the concentration of whole cholesterol in the analysis sample can be calculated from both signal values and the working curve of whole cholesterol obtained in advance and then displayed.

In calculating the cholesterol concentration, correction is made for comparison of the signal from photometric position 61 with the signal from photometric position 62 under the same conditions in the signal processing part including the central processing unit. That is, the volume of sample solution before the addition of the second enzyme reagent is different from that after the addition, and thus at least either signal must be corrected to a value obtainable when the volumes are supposed to be equal to each other, and thereafter the cholesterol concentration must be calculated.

In the present Example, the light signal from first photometric position 61 and the light signal from second photometric position 62 are to be measured only for equal wavelength light, but measurement can be carried out for different wavelength lights. In the case of different wavelength lights, measurement is carried out for one specific wavelength for a first analysis item and for another wavelength light for a second analysis item, where both one specific wavelength light and another wavelength light are taken up from the light from first photometric position 61, while another wavelength light is taken up from the light from second photometric position 62. When the present invention is applied to a rate assay method, correction should be made for a change with time in addition to the correction for the change in the volume of solution. According to the above-mentioned embodiment, analysis of two items corresponds to a single sampling, and two items can be analyzed in one reaction line.

EXAMPLE 2

Another embodiment according to the present invention will be described below, referring to FIG. 2.

Reaction disc 1 has, on the circumferential edge, a plurality of, for example, 40 light-transmitting reactor vessels 2 serving also as measuring cells, and can be rotated clockwise either by one full turn or by divisional pitch-by-pitch turn around rotary shaft 3.

Sample table 4 has a plurality of sample containers 5 on its circumferential edge, and can be intermittently rotated clockwise step by step around rotary shaft 6. Pipetting of a sample is carried out by pipette 7 provided with sampling probe 8, and the first and second enzyme reagents are poured into the vessels portion by portion by metering pumps 9 and 10. Photometer 11 is of the same multi-wavelength photometer type having a plurality of detectors as that of photometer 63 shown in FIG. 1, and arranged to face light source lamp 12 through a line of the reactor vessels so that light beam 13 from the light source can pass through the lines of reactor vessels 2, while the reaction disc is in rotation.

When the reaction disc 1 is at rest, arrangement is made so that light beam 13 of the photometer can pass through the center of a reactor vessel, for example, at the 31st position as counted clockwise from the sample-discharge position 25, to reactor vessel. A plurality of solution-discharge pipes 26 and a plurality of washing water-discharge pipes 27 are provided between the position of light beam 13 and sample-discharge position 25 so that the pipes can be inserted into or removed, from the reactor vessels. The pipes are also connected to solution-discharging device 28 and washing device 29, respectively.

Figure 3:
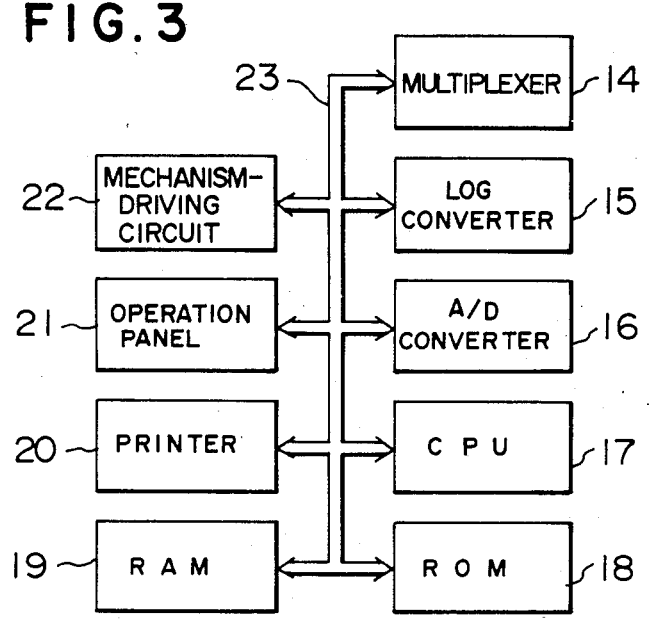
FIG. 3 is a diagram showing a signal-processing system of the embodiment of FIG. 2.

The whole structure of electric-signal-processing system 40 is comprised, as shown in FIG. 3, of multiplexer 14, logarithm conversion amplifier 15, A/D converter 16, central processing unit 17, reading-out memory 18, read-out and write memory 19, printer 20, operating panel 21 and mechanism-driving circuit 22. They are connected to bus line 23.

Now, description will be made of operations according to the present embodiment. When sample container 5 containing a sample to be analyzed, such as serum, arrives at sampling position 30, the tip end of probe (suction-and-discharge pipe) 8 of pipette 7 is inserted into sample container 5, and a predetermined amount of serum is taken up by suction and retained inside probe 8. Thereafter, probe 8 moves to discharging position 25 on reaction table 1, and then charges the serum retained therein into reactor vessel 2 at sample-receiving position 25. When the sampling operation is completed, reaction disc 1 is actuated to rotate clockwise continuously or intermittently only by such necessary angle of turn that total number plus one of the reactor vessels 2 on reaction disc 1 can pass through discharge position 25, that is, by 369°.

Owing to the rotation of reaction disc 1, reactor vessel 2 containing the sample taken up by sampling operation rests at the position only by one pitch, that is, only by 9°, far from discharge position 25, that is, first reagent-adding position 31. During the rotation of reaction disc 1, all of reactor vessels 2 on reaction disc 1 pass across light beam 13. When each of reactor vessels 2 passes through light beam 13, light absorption measurement of each sample solution is carried out by spectroscope 11. From the output of spectroscope 11, signals with wavelength now necessary for the measurement are selected by multiplexer 14, and then put into central processing unit 17 through A/D converter 16, and memorized in reading-and-writing memory 19.

Suppose that the period for rotation and rest of reaction disc 1 be, for example, 30 seconds. Operation and rest for the 30 seconds is repeated as one cycle. With repetitions of the cycle, a specific sample taken up can take a clockwise one-pitch advanced position when reaction disc 1 is at rest.

Metering pump 9 is directed to introducing the first enzyme reagent solution in tank 35 into reactor vessels, and metering pump 10 is directed to introducing the second enzyme reagent solution in tank 36 into reactor vessels. The first and second enzyme reagent solutions have the same compositions as used in the embodiment of FIG. 1. The discharge pipes 33 and 34 of metering pumps 9 and 10, respectively, are vertically movable, and a little descend when the reagent solutions are discharged. Discharge pipe 33 of metering pump 9 and discharge pipe 34 of metering pump 10 are provided over reactor vessel 2 at reagent-adding position 31, that is, the 1st position counted clockwise from discharge position 25, and over reactor vessel 2 at reagent-adding position 32, that is, the 16th position counted clockwise from discharge position 25, respectively, for example, when reaction disc 1 is at rest. That is, a given sample in reactor vessel 2 is admixed with the first enzyme reagent at reagent-adding position 31, whereby enzyme reaction of first group is initiated, and when the relevant reactor vessel reaches reagent-adding position 32 at the 15th cycle, the second enzyme reagent is added to the reactor vessel by metering pump 10, whereby the second enzyme reaction is initiated. When reactor vessel 2 moves its position at the rest of reaction disc 1 across light beam 13 to between light beam 13 and sample-receiving position 25 with further repetitions of the cycle, measurement of the given sample in the reactor vessel can be regarded as completed, and the given sample solution is discharged by suction through discharge pipe 26 by discharging device 28. Subsequently, washing water (usually distilled water) is charged into the reactor vessel through wash water discharge pipe 27 from washing device 29. At the subsequent rest of reaction disc 1, the washing water is discharged from the reactor vessel in the same manner as above ultimately, and the washed reactor vessel is reused for another sample at sample-receiving position 25 with further repetitions of the cycle. The foregoing operations are carried out by controlling the respective mechanism parts by central processing unit 17 through mechanism part-driving circuit 22 according to the program of read-out memory 18. Operating panel 21 is used for such operations as input of measuring conditions, start and discontinuation of measurement, etc.

Suppose that reaction disc 1 has a rest time of 9.5 seconds and a rotation time of 20.5 seconds in one cycle of the foregoing operation. Reaction progress of the given sample can be measured 31 times at intervals of 29.5 seconds, and thus data resulting from the measurements for 15 minutes 15 seconds are memorized in read-out and write memory 19. Central processing unit 17 operates according to the program of read-out memory 18, extracts the necessary data from 31 measurement data in read-out and write memory 19 according to the predetermined program, and gives output to printer 20 after processing such as concentration calculation, etc.

Figure 2:
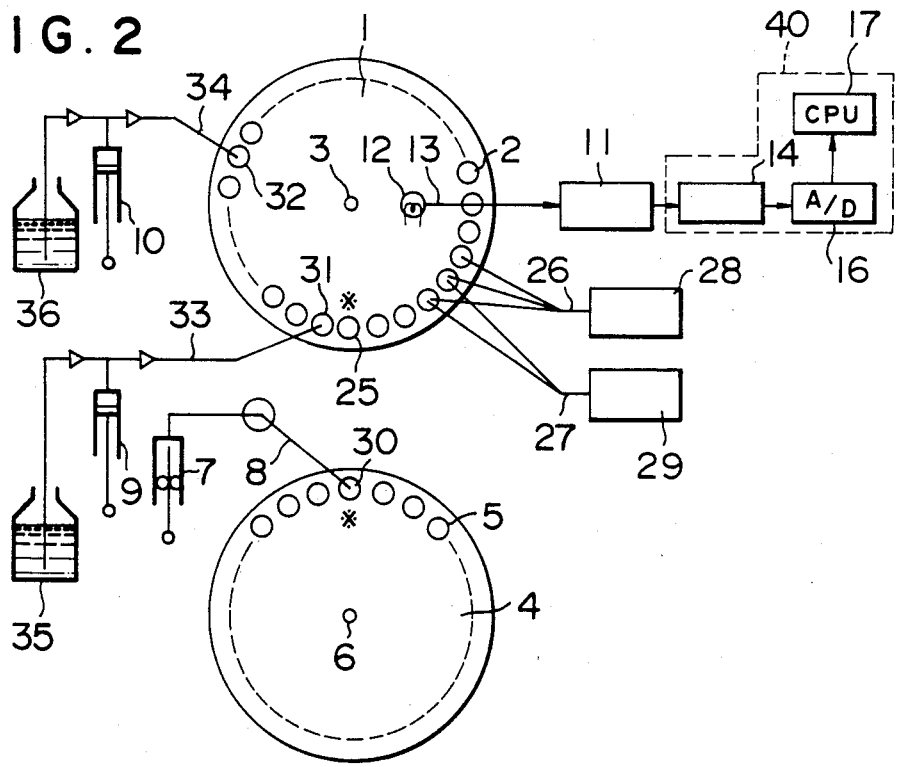
FIG. 2 is a flow diagram schematically showing a structure of another embodiment according to the present invention.

Description will be made a little in detail below, referring to an example, where the apparatus according to the embodiment of FIG. 2 is applied to analysis of two items of glucose and whole cholesterol.

On the basis of 31 absorbance data for each sample which have been memorized in read-out and write memory 19, concentration is calculated in the following manner according to predetermined program. That is, suppose that 16th absorlance datum be $E_{16}$ and 31th datum $E_{31}$.

Glucose concentration $Y_1$ will be expressed as follows:

$$Y_1 = \frac{C_S}{E_{16}^S - E_{16}^O} (E_{16} - E_{16}^O)$$

Whole cholesterol concentration $Y_2$ will be expressed as follows:

$$Y_2 = \frac{C_S'}{E_{31}^S - \kappa E_{16}^S} (E_{31} - \kappa E_{16})$$

wherein $C_S$ and $C_S'$ are glucose concentration and cholesterol concentration, respectively, of standard solution used for preparing a working curve, and memorized as input from operating panel 21; $E_{16}^O$ is 16th data for the reagent blank; $E_{16}^S$ and $E_{31}^S$ are 16th data for glucose and 31th data for whole cholesterol of standard solution; K is a correction factor for the amount of solution and in this case, K=505/555 because the amount sample is 5 µl, that of first enzyme reagent solution 500 µl and that of second enzyme reagent solution 50 µl.

The present invention is applicable not only to the analysis of two components but also to that of three or more components. For example, in order to analyze three components by application of the apparatus of the embodiment shown in FIG. 2, a third enzyme reagent-adding position is provided between second reagent-adding position 32 and light beam 13. For example, in analyzing three components of glucose, whole cholesterol and neutral fat, after the above-mentioned analysis of two components of glucose and the whole cholesterol, lipoprotein lipase and glycerol oxidase are added as third reagents to the reaction solution to complete the reactions of formulae (4), (5) and (8), and the concentration of neutral fat is calculated from the difference between the absorbances before and after the addition of the third reagents.

Figure 4:
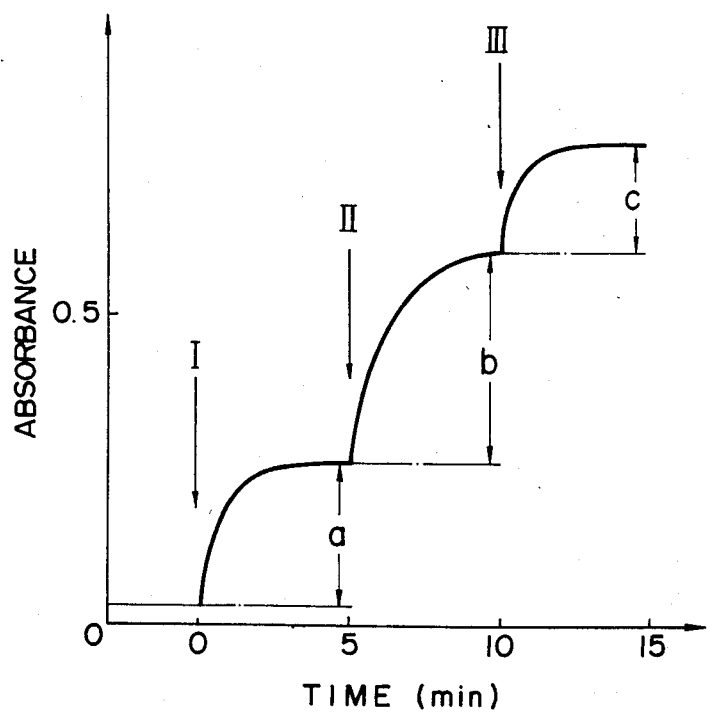
FIG. 4 is a diagram showing the measurement of three analysis items in one sample.

When the absorbance of the reaction solution in this case is traced with time, the results will be as given in FIG. 4. The magnitude of a, b and c in FIG. 4 are proportional to the respective concentrations of glucose, whole cholesterol and neutral fat.

I, II and III in FIG. 4 show the points of time of adding the first, second and third enzyme reagents, respectively.

Although in embodiments shown in FIG. 1 and FIG. 2, the same measuring wavelength is used for analyzing two components, different measuring wavelengths can be selected for analyzing the first component and for analyzing the second component.

In this case, data with two different wavelengths can be obtained as 16th absorbance datum, or 15th absorbance datum $E_{15}$ may be obtained as data for the first component with a wavelength different from the measuring wavelengths for $E_{16}$ and $E_{31}$.

In this case, concentration $Y_1$ of the first component can be calculated as follows:

$$Y_1 = \frac{C_S}{E_{15}^S - E_{15}^O} (E_{15} - E_{15}^O)$$

Concentration $Y_2$ of the second component can be expressed by the following equation:

$$Y_2 = \frac{C_S'}{E_{31}^S - \kappa E_{16}^S} (E_{31} - \kappa E_{16})$$

A few embodiments of measuring the activity of enzyme contained in a sample by rate assay method will be described below. The analytical apparatus shown in FIG. 2 will be used in the following embodiments.

EXAMPLE 3

In the present embodiment, a method for analyzing two analysis items of lactate dehydrogenase (LDH) and leucine aminopeptidase (LAP) contained in a serum sample is applied to the apparatus in FIG. 2. As examples of suitable reagent compositions in this case, solutions having the following compositions are used, where NADH means reduced form nicotineamide adenine dinucleotide.

Composition of first reagent solution:

| Pyruvic acid | 0.6 m moles/liter |
|---|---|
| Phosphate buffer (pH 7.5) | 50 m moles/liter |
| NADH | 0.18 m moles/liter |

Composition of second reagent solution:

| L-leucine-p-nitroanilide | 3.2 m moles/liter |
|---|---|
| Phosphate buffer (pH 7.5) | 400 m moles/liter |

Measuring conditions for the apparatus are as follows:

| Amount of sample | 20 μl |
|---|---|
| Amount of first reagent | 500 μl |
| Amount of second reagent | 250 μl |
| Reaction temperature | 25° C. |
| Measuring wavelengths 1 | 340 nm/376 nm |
| Measuring wavelengths 2 | 405 nm/505 nm |

When the above-mentioned first and second reagents are placed in solution tank 35 for metering pump 9 and solution tank 36 for metering pump 10, respectively, and sample table 4 is loaded with the sample, then an instruction "start analysis" is given from operating panel to actuate the apparatus.

Reaction in reactor vessel 2 is traced. Reaction proceeds according to the following formula (9) from the point of time of mixing the sample with the first reagent solution.

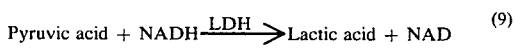

(9)

The second reagent is subsequently added thereto after 7.5 minutes, and reaction starts according to the following formula (10) in parallel with the reaction according to the above formula (9).

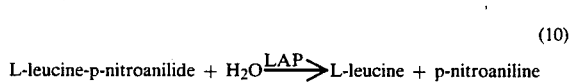

(10)

The rate of reaction of formula (9) can be determined by tracing the absorbance of NADH according to the single beam dual-method at 340 nm/376 nm, and is proportional to the activity of LDH. The rate of reaction of formula (10) can be determined by tracing formation rate of p-nitroaniline through the absorbance according to the single beam dual-wavelength method, and is proportional to the activity of LAP.

In the case of the combined use of these two pairs of wavelengths, as shown in FIG. 5, the measuring wavelengths are changed from 340 nm/376 nm for the measurement of the reaction by the first reagent to 405 nm/505 nm at the point of time of adding the second reagent. After the change, the components for the reaction of formula (9) contain no such components that substantially absorb the relevant wavelengths, and thus only the reaction of formula (9) can be traced. In FIG. 5, A is the point of time of adding the first reagent. Between the point of time A and the point of time B, LDH reaction takes place, and after the point of time B, LAP reaction takes place.

EXAMPLE 4

Description will be made below of another embodiment of a method for analyzing two analysis items of glutamic oxalacetic transaminase (GOT) and glutamic pyruvic transaminase. As examples of suitable reagent compositions in this case, solutions of the following compositions can be used.

Composition of first reagent solution:

| α-Ketoglutaric acid | 18 m moles/liter |
|---|---|
| L-aspartic acid | 200 m moles/liter |
| NADH | 0.18 m moles/liter |
| MDH | ≧0.6 U/ml |

| -continued | |
|---|---|
| LDH | ≧1.2 U/ml |
| Phosphate buffer (pH 7.4) | 80 m moles/liter |

Composition of second reagent solution:

| L-alanine | 6.4 m moles/liter |
|---|---|
| Phosphate buffer (pH 7.4) | 80 m moles/liter |

The measurement conditions for the apparatus are as follows:

| Amount of sample | 20 μl |
|---|---|
| Amount of first reagent | 350 μl |
| Amount of second reagent | 50 μl |
| Reaction temperature | 25° C. |
| Measurement wavelengths | 340 nm/376 nm |

When said method is applied to the apparatus in FIG. 2, the reactions of formulae (11) and (12) proceed after the addition of the first reagent.

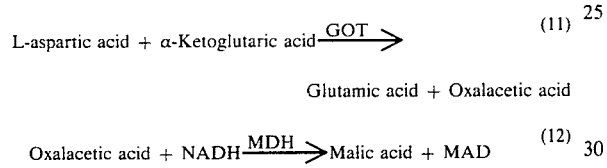

When the second reagent is subsequently added, the reactions of formulae (13) and (9) proceed in parallel with the reactions of formulae (11) and (12).

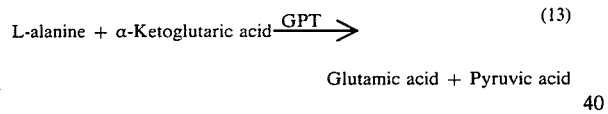

The rate of the reaction of formula (11) is proportional to GOT concentration in the sample and a decreasing rate of NADH in the reaction of formula (12) coupled with the reaction of formula (11), and a decreasing rate of NADH can be determined from the absorbances at 340 nm/376 nm. That is to say, as shown in FIG. 6, an absorbance change per minute, $X_1$, can be obtained from 15 absorbance data in 15 cycles for 7.5 minutes after the addition of the first reagent, and the activity $Y_1$ of GOT can be obtained as the following formula:

$$Y_1 = \frac{X_1 \times V_1 \times 1{,}000}{\epsilon \times d \times v} \quad (14)$$

wherein $V_1$ is a total volume of reaction solution (V=370 μl); $\epsilon$ is a molecular absorption coefficient ($\epsilon$=4.20); d is length of the optical path (d=1 cm); and v is a volume of samples (v=20 μl).

Thus, $Y_1$ in formula (15) will be as follows:

$$Y_1 = X_1 \times \frac{370 \times 1{,}000}{4.20 \times 1 \times 20} \quad (15)$$

$$= X_1 \times 4{,}405$$

An absorbance change per minute, $X_2$, can be obtained from 15 absorbance data after the addition of the second reagent and is proportional to the sum ($Y_2$) of the activities of GOT and GPT. That is to say, $$Y_2 = \frac{X_2 \times V_2 \times 1{,}000}{\epsilon \times d \times v} \quad (16)$$

and since $V_2$=420 μl, $$Y_2 = X_2 \times \frac{420 \times 1{,}000}{4.20 \times 1 \times 20} \quad (17)$$

$$= X_2 \times 5{,}000$$

Accordingly, the activity $Y_3$ of GPT can be obtained from the following equation:

$$Y_3 = Y_2 - Y_1$$

In FIG. 6, A is the point of time for adding the first reagent, and B is the point of time for adding the second reagent.

What is claimed is:

1. An apparatus for optically analyzing at least two analytical items, which comprises:
   a reactor turntable provided with a plurality of reactor vessels on a circumferential edge thereof;
   a first dispenser for charging a first enzyme reagent into the reactor vessels at a first position over the circumferential edge of said turntable;
   a second dispenser for charging a second enzyme reagent into the reactor vessels at a second position over the circumferential edge of said turntable;
   a spectroscope for light absorption measurement of a sample solution in the reactor vessels by detecting a light beam passing through the reactor vessels at a third position on the circumferential edge of said turntable;
   a sample-feeding means for feeding a sample to the reactor vessels at a fourth position on the circumferential edge of said turntable; and
   control means for providing analysis of at least two analytical items in the sample solution in a given reactor vessel of said reactor vessels, said control means including means for alternately actuating the first dispenser, the second dispenser, and the sample feeding means so as to feed first enzyme reagent, second enzyme reagent, and sample, respectively, to the given reactor vessel while the reactor turntable is at rest and for turning the reactor turntable by a one pitch difference with respect to the given reactor vessel and actuating the spectroscope during the turning; said control means further including (1) means for analyzing a first analytical item in the sample solution in the given reactor vessel on the basis of an output of light absorption measurement of the sample solution by the spectroscope after the addition of the first enzyme reagent from the first dispenser to the sample solution, and (2) means for analyzing a second analytical item in the sample solution in the given reactor vessel after the addition to the given reactor vessel of the second enzyme reagent from the second dispenser, said means for analyzing a second analytical item conducting said analysis of the second analytical item from a difference between (a) said output of light absorption measurement and (b) another output of light absorption measurement of the sample solution in the given reactor vessel by the spectroscope after the addition to the given reactor vessel of the second enzyme reagent.

2. An apparatus according to claim 1, wherein the means for turning the reactor turntable is a means for turning the reactor turntable one full turn plus one pitch.

3. An apparatus according to claim 1, further comprising a light beam source for providing said light beam, the light beam source being located within the circumferential edge of said reactor turntable.

4. An apparatus according to claim 1, wherein said spectroscope includes means for providing an output representing a measurement when each reaction vessel of the reactor turntable is at said third position during the turning of the turntable.

5. An apparatus according to claim 1, wherein said control means includes means for adjusting at least one of the output of light absorption measurement after the first enzyme reagent is charged to the given reactor vessel and the output of light absorption measurement after the second enzyme reagent is charged to the given reactor vessel due to a degree of dilution of the solution resulting from charging both the first enzyme reagent and the second enzyme reagent to the given reactor vessel.

6. An apparatus according to claim 1, wherein said means for analyzing a first analytical item and said means for analyzing a second analytical item respectively conduct the first and second analysis utilizing a working curve for the first analytical item and a working curve for the second analytical item, respectively.

7. An apparatus according to claim 1, wherein the means for actuating the spectroscope during the turning is a means for causing light absorption measurement by the spectroscope of each of the reactor vessels, with each light absorption measurement providing an output from the spectroscope, whereby a plurality of outputs from the spectroscope are provided, and wherein the control means further includes means for selecting said output of the spectroscope measuring the given reactor vessel after the first enzyme reagent is charged to the given reactor vessel, and for selecting said output of the spectroscope measuring the given reactor vessel after the second enzyme reagent is charged to the given reactor vessel, from the plurality of outputs from the spectroscope.

8. An apparatus according to claim 7, wherein the spectroscope is a multi-wavelength spectrometer, and the means for selecting includes means for selecting the output of the spectrometer at different measuring wavelengths.

9. An apparatus according to claim 8, wherein the means for selecting the output at different measuring wavelengths includes means for selecting the output of the spectrometer after the first enzyme reagent is charged to the given reactor vessel at a different measuring wavelength than the output of the spectrometer after the second enzyme reagent is charged to the given reactor vessel.

10. An apparatus according to claim 7, wherein the means for selecting selects the output at the same measuring wavelength.

11. An apparatus according to claim 1, further including at least a third dispenser for charging, respectively, at least a third enzyme reagent at at least a fifth position, respectively, over the circumferential edge of said turntable, and wherein the control means further includes means for analyzing respective further analytical items in solution in the given reactor vessel from an output of the spectroscope after the at least a third enzyme reagent is charged to the given reactor vessel.

12. An apparatus according to claim 11, wherein said control means further includes means for analyzing a third analytical item in the sample solution in the given reactor vessel after the addition of the third enzyme reagent from the third dispenser, the means for analyzing a third analytical item conducting the analysis from a difference between (a') the output of the spectroscope after the at least a third enzyme reagent is charged to the given reactor vessel and (b') the output of the spectroscope prior to charging of the at least a third enzyme reagent.

13. A method for optically analyzing at least two analytical items, which comprises the steps of:
conveying a transparent container containing a sample containing at least two analytical items to be measured to a position where a first enzyme reagent solution is to be added;
preparing a first reaction solution by introducing a first enzyme reagent solution into said container so as to cause a first reaction;
conveying said container containing the aforesaid first reaction solution, thereby passing the container across an optical path of a photometer so as to be able to measure light absorption by the first reaction solution;
conducting a first optical measurement for obtaining a first signal corresponding to optical characteristics of the aforesaid first reaction solution when the container is irradiated with light, said first signal corresponding to light absorption by the first reaction solution;
conveying said container containing the aforesaid first reaction solution, after the first optical measurement, to a position where a second enzyme reagent solution is to be added;
preparing a second reaction solution by introducing a second enzyme solution into said container still containing the first reaction solution so as to cause a second reaction;
conveying said container containing the aforesaid second reaction solution, thereby passing the container across an optical path of said photometer so as to be able to measure light absorption by the second reaction solution;
conducting a second optical measurement for obtaining a second signal corresponding to optical characteristics of the second enzyme reaction solution when the container is irradiated with light, said second enzyme signal corresponding to light absorption by the solution in the container after forming the second reaction solution;
measuring a first analytical item on the basis of the first signal obtained in the first optical measurement; and
measuring a second analytical item on the basis of the signals obtained in the first and second optical measurement, the measuring of the second analytical item including finding a difference between said second signal and said first signal.

14. The method according to claim 13, wherein one of the first and second signals is adjusted in accordance with a degree of dilution of the first reaction solution caused by the introduction of the second enzyme reagent solution.

15. The method according to claim 13, wherein said transparent container is one of a plurality of transparent containers conveyed.

16. The method according to claim 15, wherein said plurality of transparent containers are located on a circumferential edge of a reactor turntable.

17. An apparatus for optically analyzing at least two analytical items, which comprises:
a plurality of reactor vessels;
a first dispenser for charging a first enzyme reagent into the reactor vessels;
a second dispenser for charging a second enzyme reagent into the reactor vessels;
a spectroscope for light absorption measurement of a sample solution in the reactor vessels by detecting a light beam passing through the reactor vessels;
a sample-feeding means for feeding a sample to the reactor vessels; and
control means for providing analysis of at least two analytical items in the sample solution in a given reactor vessel of the said reactor vessels, said control means including means for alternately actuating the first dispenser, the second dispenser, and the sample feeding means so as to feed first enzyme reagent, second enzyme reagent and sample, respectively, to the given reactor vessel while the given reactor vessel is at rest and for moving the reactor vessels and actuating the spectroscope during the moving; said control means further including (1) means for analyzing a first analytical item in the sample solution in the given reactor vessel from an output of light absorption measurement of the sample solution by the spectroscope after the addition of the first enzyme reagent from the first dispenser to the sample solution, and (2) means for analyzing a second analytical item in the sample solution in the given reactor vessel after the addition to the given reactor vessel of the second enzyme reagent from the second dispenser, said means for analyzing a second analytical item conducting said analysis of the second analytical item from a difference between (a) said output of light absorption measurement and (b) another output of light absorption measurement of the sample solution in the given reactor vessel by the spectroscope after the addition to the given reactor vessel of the second enzyme reagent.

18. An apparatus according to claim 17, wherein the plurality of reactor vessels are connected in a chain and pass along a path, wherein the first dispenser charges the first enzyme reagent at a first position on said path, wherein the second dispenser charges the second enzyme reagent at a second position on said path, wherein the spectroscope detects a light beam passing through the reactor vessels at a third position on said path, and wherein the sample-feeding means feeds the sample at a fourth position on said path.

19. An apparatus according to claim 17, wherein said control means includes means for adjusting at least one of the output of light absorption measurement after the first enzyme reagent is charged to the given reactor vessel and the output of light absorption measurement after the second enzyme reagent is charged to the given reactor vessel due to a degree of dilution of the solution resulting from charging both the first enzyme reagent and the second enzyme reagent to the given reactor vessel.

* * * * *